United States Patent [19]

Hagen et al.

[11] Patent Number: 5,071,610
[45] Date of Patent: Dec. 10, 1991

[54] METHOD OF MAKING A CONTROLLED PORE COMPOSITE POLYTETRAFLUOROETHYLENE

[75] Inventors: Donald F. Hagen, Woodbury; Craig G. Markell, White Bear Township, Ramsey County; William V. Balsimo, Afton; Louis A. Errede, North Oaks, all of Minn.

[73] Assignee: Minnesota Mining and Manufacturing Company, St. Paul, Minn.

[21] Appl. No.: 639,515

[22] Filed: Jan. 10, 1991

Related U.S. Application Data

[63] Continuation-in-part of Ser. No. 484,184, Feb. 23, 1990, abandoned.

[51] Int. Cl.$^5$ .......................... B01D 15/08; B29D 9/00
[52] U.S. Cl. .................... 264/120; 264/122; 264/127; 264/DIG. 47; 210/635; 210/656; 210/658; 210/198.2; 210/198.3; 210/502.1
[58] Field of Search ............... 264/49, 108, 120, 122, 264/127, 175, 349, DIG. 47; 51/295, 298 R; 210/635, 656, 658, 198.2, 198.3, 502.1; 428/305.5, 317.9; 435/803

[56] References Cited

U.S. PATENT DOCUMENTS

| | | | |
|---|---|---|---|
| 3,005,795 | 10/1961 | Busse et al. | 260/45.5 |
| 3,281,511 | 10/1966 | Goldsmith | 264/49 |
| 3,315,020 | 4/1967 | Gore | 264/120 |
| 3,383,092 | 5/1968 | Cazier | 253/40 |
| 3,407,096 | 10/1968 | Landi | 136/86 |
| 3,407,249 | 10/1968 | Landi | 264/49 |
| 3,533,930 | 11/1966 | Lawton et al. | 204/159.15 |
| 3,556,161 | 8/1966 | Roberts | 138/141 |
| 3,864,124 | 2/1975 | Breton et al. | 75/212 |
| 4,153,661 | 5/1979 | Ree et al. | 264/120 |
| 4,194,040 | 3/1980 | Breton et al. | 428/308 |
| 4,373,519 | 2/1983 | Errede et al. | 128/156 |
| 4,460,642 | 7/1984 | Errede et al. | 428/283 |
| 4,565,663 | 1/1986 | Errede et al. | 264/120 |
| 4,722,898 | 2/1988 | Errede et al. | 435/180 |
| 4,810,381 | 3/1989 | Hagen et al. | 210/502.1 |
| 4,863,604 | 9/1989 | Lo et al. | 210/490 |
| 4,871,671 | 10/1989 | Errede et al. | 435/182 |
| 4,882,113 | 11/1989 | Tu et al. | 264/127 |
| 4,906,378 | 3/1990 | Hagen et al. | 210/635 |
| 4,971,697 | 11/1990 | Douden et al. | 210/502.1 |
| 4,971,736 | 11/1990 | Hagen et al. | 264/22 |

FOREIGN PATENT DOCUMENTS

993193  3/1963  United Kingdom ............. 210/198.2

OTHER PUBLICATIONS

*Design News,* Feb. 9, 1987 (Cahners Publishing Company), "Particulates Captured/Carried by Fibrillated PTFE", 2 pages.
"Membrane Approach to Solid Phase Extractions", *Analytica Chimica Acta,* 236 (1990) 157-164.

*Primary Examiner*—Ernest G. Therkorn
*Attorney, Agent, or Firm*—Gary L. Griswold; Walter N. Kirn; Lorraine R. Sherman

[57] ABSTRACT

A composite article having controlled void volume and mean pore size comprises:
(a) polytetrafluoroethylene (PTFE) fibril matrix, and
(b) insoluble, non-swellable sorptive particles enmeshed in said matrix, the ratio of non-swellable sorptive particles to PTFE is in the range of 40:1 to 1:4 by weight, the composite article having a porosity in the range of 30 to 80 percent void volume and a mean pore size in the range of 0.3 to 5 micrometers, preferably with at least 90 percent of pores having a size less than 3.6 micrometers.

The article is prepared by incorporating lubricant in the precursor admixture in an amount sufficient to exceed the lubricant sorptive capacity of the particles by at least 3 weight percent and up to an amount at which the mass loses its integrity.

20 Claims, 3 Drawing Sheets

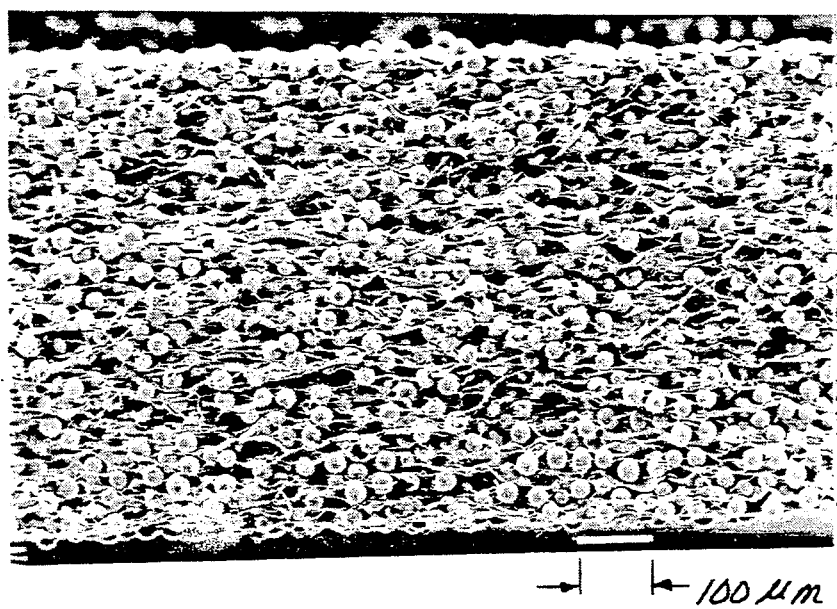

METHOD OF MAKING A CONTROLLED PORE COMPOSITE POLYTETRAFLUOROETHYLENE

This is a continuation-in-part of application Ser. No. 07/484,184, filed Feb. 23, 1990.

FIELD OF THE INVENTION

This invention relates to articles which are composite structures and a method therefor, the articles comprising a polytetrafluoroethylene (PTFE) fibril matrix having controlled pore sizes and void volumes. The composite structures are useful as selective sorptive or reactive media for applications in separations, purifications, diagnostics, environmental extractions, clinical extractions, catalysis, exotic laminates, and the like.

BACKGROUND OF THE INVENTION

Separation science and purification are well known in the art and two journals dedicated to this field are "Separation Science and Technology" and "Separation and Purification Methods", both published by Marcell Dekker, N.Y., N.Y. Numerous books dedicated to this topic are also well known in the art. Eventually, the chemical practitioner needs to rely on one or more separation and/or purification methods involving sorption techniques. These techniques provide a means comprising a sorptive medium for resolving (i.e., separating and analyzing) mixtures by selectively sorbing and desorbing components in the mixture.

Recently sorptive media in a polytetrafluoroethylene (PTFE) matrix have been described in separation science.

U.S. Pat. No. 4,810,381 and related U.S. Pat. Nos. 4,906,378 and 4,971,736 describe a composite chromatographic article comprising a polytetrafluoroethylene fibril matrix, and non-swellable sorptive particles enmeshed in the matrix.

U.S. Pat. No. 4,153,661 discloses a method of making a polytetrafluoroethylene composite sheet comprising a PTFE matrix with substantially water insoluble particulate materials dispersed therein. The resulting sheet is extremely pliable, akin to doe skin. It is said to be useful as an electronic insulator or a semi-permeable membrane.

U.S. Pat. No. 4,373,519 teaches a composite wound dressing comprising a PTFE matrix with water-swellable hydrophilic absorptive particles enmeshed in the matrix, and, optionally, a partially occlusive film coated on one surface of the matrix. The sheets are described as conformable and chamois-like.

U.S. Patent Nos. 4,565,663 and 4,460,642, which are related to U.S. Pat. No. 4,373,519 (a division of a continuation-in-part application and a continuation-in-part, respectively) disclose water-swellable composite sheets having a PTFE matrix in which are enmeshed water-swellable hydrophilic absorptive particles. The sheets are described as conformable and chamois-like. Certain water-swellable cation exchange resins in the composite sheets can be used as chromatographic materials.

U.S. Pat. Nos. 4,722,898 and 4,871,671 disclose a composite article comprising a polytetrafluoroethylene fibril matrix in which are enmeshed viable animal, bacterial, fungal, or yeast cells.

The background art taught several formulations for blending an aqueous PTFE dispersion with various additives and/or adjuvants, designed for specific purposes. The background art also taught that blending of these particles or additives with an aqueous PTFE dispersion to form a mass having a putty-like or dough-like consistency and only specified addition of sufficient lubricant to exceed the sorptive capacity of the particles (see e.g., U.S. Pat. No. 4,810,381, column 6, lines 22-30; see also U.S. Pat. Nos. 4,373,519, 4,460,642 and 4,565,663). Moreover, U.S. Pat. No. 4,810,381 provides a guide and a caution when sorptive capacity is exceeded (see col. 6, lines 25-33).

U.S. Pat. Nos. 3,407,096, 3,407,249, and 3,556,161 teach incorporation of extractable or leachable organic and inorganic filler particles at various levels and particle sizes in composite sheets to provide the desired porosity for their applications. U.S. Pat. Nos. 3,864,124, 4,194,040, 3,383,092, 3,005,795, and 3,533,930 teach dry or lubricant-free processes. U.S. Pat. No. 3,281,511 describes use of leachable filler particles (colloidal alumina, sodium chloride, and ammonium carbonate), which are removed after making the article, to create porosity by an extraction/leaching method. In addition, the resulting fibrillated matrix is PTFE and does not contain sorptive particulate for separation purposes.

U.S. Pat. No. 3,315,020 and GB 993,193 teach preparation of PTFE sheeting by an extrusion process and then performing rolling or stretching. Lubricant fluid which will mix with polytetrafluoroethylene, e.g., naphtha, gasoline, kerosene, alcohols, glycerol, and most organic liquids can be used and up to 50 volume percent filler. The sheeting is used to mold shaped articles.

SUMMARY OF THE INVENTION

Briefly, the present invention provides a PTFE composite article comprising:
(a) a polytetrafluoroethylene (PTFE) fibril matrix, and
(b) insoluble, non-swellable sorptive particles enmeshed in said matrix, the ratio of non-swellable sorptive particles to PTFE is in the range of 40:1 to 1:4 by weight, the composite article having a porosity in the range of 30 to 80 percent void volume, and a mean pore size in the range of 0.3 to 5.0 micrometers.

In another aspect, the present invention provides a method for controlling porosity and mean pore size in fibrillated, semi-rigid, composite articles such as sheets of PTFE having chromatographically active non-swellable sorptive particles enmeshed, and evenly distributed but not adhered, therein. These articles can be prepared from chromatographically active non-swellable sorptive particles and a PTFE emulsion via an improvement of the work intensive procedures described in U.S. Pat. No. 4,153,661, so as to increase porosity in the fibrillated article. The improved method for providing a composite sheet comprises the steps of:
a) admixing lubricant with a blend comprising insoluble, non-swellable, sorptive particles and polytetrafluoroethylene to form a soft dough-like mass, the lubricant being present in an amount to exceed the lubricant sorptive capacity of the particles by at least 3 weight percent and up to an amount at which the mass loses its integrity, said mass having a cohesive consistency, and the ratio of insoluble particles to PTFE being in the range of 40:1 to 1:4;
b) intensively mixing said mass at a temperature and for a time sufficient to cause initial fibrillation of said PTFE particles;
c) biaxially calendering said mass between gaps in calendering rolls maintained at a temperature and for a time, while closing the gap between the calendering rolls with each successive calendering operation, to cause additional fibrillation of said PTFE particles to form a self-supporting tear-resistant sheet.

Preferably, the improved method involves increasing the amount of lubricant present during processing so that it is at least 3 weight percent and up to 200 weight percent in excess of that required to exceed the sorptive capacity of the particles for the lubricant, more preferably at least 5 weight percent and up to 200 weight percent, even more preferably at least 25 and up to 200 weight percent, and most preferably at least 40 and up to 150 weight percent in excess of that required to exceed the sorptive capacity of the particles for the lubricant.

In a further aspect, the present invention provides a general method for using particle loaded membranes for analyses in clinical, biological, and environmental areas, the void volume of the membranes being controlled by the amount of lubricant used in fabrication of the article. The membranes are useful for both size/filtration separations and sorptive chromatographic separations at the molecular level.

In these utilities the article is advantageous in that even distribution of particulate in the PTFE matrix eliminates undesirable channeling which can be experienced using prior art packed columns/beds with solutions flowing therethrough. Separation and chromatographic articles of this invention are useful in chemical and biochemical separations/purifications.

In this application:

"controlled porosity" means an open structure containing voids designed to obtain optimum flow of liquids and gases with efficient chromatographic performance; i.e., for efficient separation and resolution of a mixture into its component parts;

"void volume" means the vacancies in the structure of a composite;

"matrix" means an open-structure entangled mass of microfibers;

"hydrophobic particles" mean particles with low surface polarity, i.e. in the range of 0.1–0.5;

"semi-rigid" means flexible, dimensionally stable, and non-conformable; creasing results in cracking;

"ceramic" means nonmetallic, inorganic materials;

"normal phase system" means a more polar stationary phase with a less polar moving phase;

"reverse phase system" means a less polar stationary phase with a more polar moving phase;

"non-swellable particulate" means particulate having a change in volume of less than 0.5, preferably less than 0.1, most preferably less than 0.01, where $V_g$ is the volume of the particulate when swollen and $V_o$ is the volume of the dry particulate, wherein
change in volume $= (V_g - V_o)/V_o$;

"particles" or "particulate" means solid shapes (not including PTFE) having a diameter 0.1 to 200 micrometers, preferably 5 to 40 micrometers, with an aspect ratio of 1 to 1,000,000, in addition to particles as defined below;

"property modifying particles" means those particles which are substantially non-sorptive in separation and chromatographic applications and which modify the surface energy of the article; for example, such particles can render the article hydrophilic, of greater tensile strength, or make it more easily fibrillatable;

"net surface energy" means the sum of polar and non-polar surface energies;

"self-supporting" means that no rigid backing support is needed for the article;

"tear-resistant sheet" means will not tear in a linear manner;

"sorbent" or "sorptive" means capable of taking up and holding by either absorption or adsorption;

"lubricant" means water-based fluids and organic liquids or a combination thereof which are used to facilitate making of the composite article; and "lubricant sorptive capacity" means that amount of lubricant required to saturate a mass of particles.

The present invention provides a porous, fibrillated PTFE containing article, and a process therefor. The porosity and void volume of the article are controlled by the amount of lubricant used in the fabrication of the article. It has been found that the amount of lubricant used during the fibrillation process is directly related to and controls percent void volume in the final article and also the mean pore size. As the amount of lubricant is increased, the void volume and mean pore size increases as is shown in FIG. 3. Critical features in articles used in separation processes are void volume and pore size because they control flow-through times in filtration and solvent migration rates in planar chromatography. The article is useful for analytical and preparative purposes in separation science, and in analyses in the fields of clinical, biological and environmental sciences.

Heretofore, the separation scientist skilled in the art selected a chromatographic sorptive particulate which operated in either a normal phase mode or in a reverse phase mode or prepared an aggregation thereof, depending on the nature of the material to be separated and/or purified. The particulate was packed into a tube for column chromatography or coated on a substrate such as a glass or plastic plate for planar chromatography (TLC which usually uses a "glue" or binder particulate such as hydrated calcium sulfate to hold the particles in place).

The present invention teaches practical and efficient chromatographic articles and a process therefor which can be operated in either normal or reverse phase modes or a combination of both in membrane or sheet form as well as in column form. Performance in these forms is determined by controlled porosity of the chromatographic material which is prepared using specific levels of lubricant and by controlled ratios of the PTFE matrix and normal/reverse phase sorptive particles that are intimately present in fabricated chromatographic articles of this invention. Increase in the level of lubricant during fabrication of the PTFE/particulate article results in increase in void volume and mean pore size in the final article. No teachings have been found in the background art wherein the level of lubricant is controlled to obtain controlled porosity as described in this invention. The effect of lubricant, it is now recognized, is to provide a non-compressible medium wherein the particulate are held apart, one from another, which creates pores in the article. Heretofore, the role of lubricant was not recognized and frequently excipients such as salt, sugar, or ammonium bicarbonate were incorporated in the PTFE matrix and dissolved out with solvent to provide vacancies or pores.

Control of lubricant level provides predictable and reproducible porosity and performance characteristics (e.g., solvent wicking time, fluid flow-through). Those skilled in the separation art recognize the importance of surface area of the particles, particle packing density, and uniformity of particle size in producing a separations medium. For the first time, it is now disclosed that lubricant level in the processing of the PTFE containing article of the present invention has a direct and controlling effect in providing superior and consistent separations properties.

Controlling the level of lubricant during fibrillation of the PTFE composite article controls the pore size and void volume in the final article. Increasing the amount of lubricant so that it exceeds the lubricant sorptive capacity of the particulate by at least 3 wt. percent, preferably by at least 5 wt. percent, more preferably by at least 25 wt. percent, and most preferably by at least 40 wt. percent and up to 200 wt. percent, provides mean pore sizes in the final article in the range of 0.3 micrometer to 5.0 micrometer, preferably 0.4 to 5.0 micrometers, more preferably 0.5 to 5.0 micrometers, and preferably with at least 90 percent of pores having a size less than 3.6 micrometers, more preferably with at least 50 percent of pores being less than 2.5 micrometers in size. The void volume and mean pore size vary directly as the amount of lubricant present during the fibrillation process, all other variables remaining constant including amounts of PTFE and particulate (type and size), mixing time, temperature, number of folds during calendering, size of gaps between rollers, and type of lubricant. These other variables can affect porosity but do not have the precise controlling effect of lubricant. The amount of lubricant useful can vary depending on the nature of the particulate, and it has been found that increasing the amount of lubricant during processing increases the total pore volume and the mean pore size. Increased pore volume and increased mean pore size result in reduced solvent wicking time and decreased fluid flow-through times.

We have found that accurately controlling the amount of lubricant during preparation of articles of the invention has provided articles having unexpected and very desirable properties. As noted above, the composite articles of the invention exhibit superior separation properties with an increase in solvent wicking and filtration velocity.

What the background art has not shown but what we have demonstrated is the ability to control the porosity of an article comprising PTFE-enmeshed particulates without the use of leachable materials. We have discovered that the amount of lubricant chosen can be used to control porosity and void volume in a precise manner not recognized heretofore. This is of particular advantage in use of the article where flow and flow rate of a fluid through the article is involved as in separation applications involving extractions, separations, and purifications.

BRIEF DESCRIPTION OF THE DRAWING

FIG. 1 is a photomicrograph (enlarged 100×) of a composite article according to the present invention having a matrix of PTFE fibrils in which are enmeshed chemically and/or physically active, sorptive, non-swellable particles.

DETAILED DESCRIPTION OF THE DRAWING

FIG. 1 is a photomicrograph of a 0.5 mm thick cross section of a composite article of the invention showing fibrillated PTFE and 15 micrometer diameter cation exchange particles. This formulation contains 20 percent PTFE and 80 percent particulate on a weight percent basis and was prepared by the work intensive procedure described in Example 1. The PTFE fibrils entrap particulate and the small fibril diameter, low surface area, and sorptive inertness obstruct very few of the sorptive sites of the particulate. The sum of the spaces between the particles constitutes the void volume of the article. In this case, the void volume was approximately 60 percent of the volume of the article.

Figure 2:
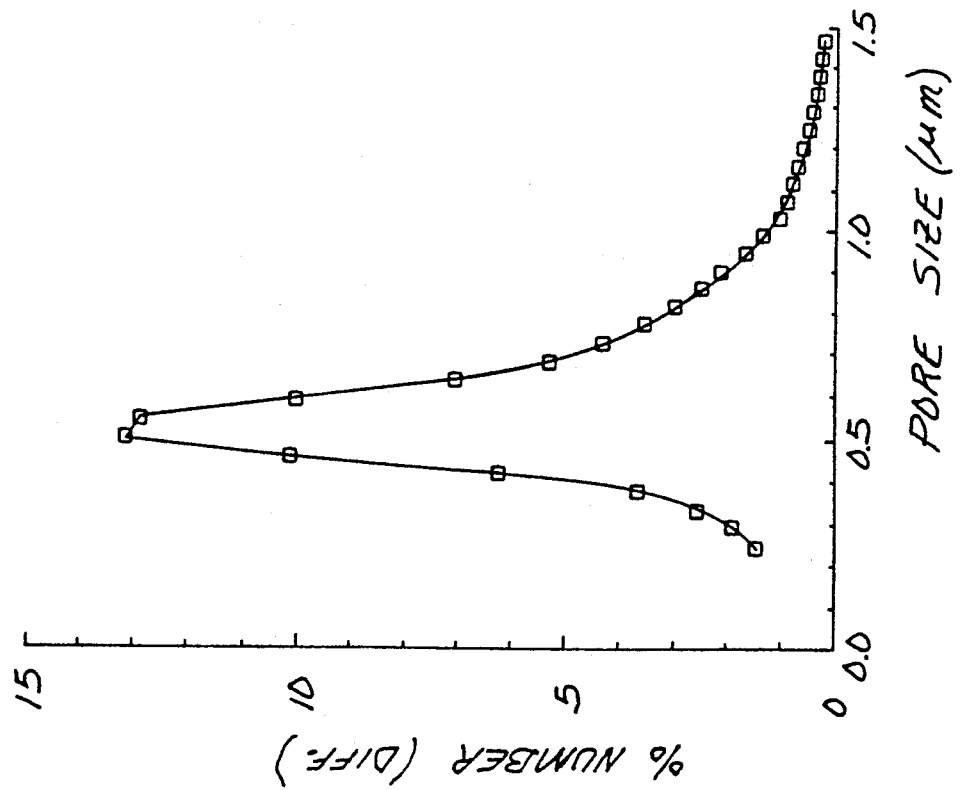
FIG. 2 is a plot of the number percent of pores versus pore size for a composite sheet of the present invention.

FIG. 2 is a plot of the number percent pore size distribution of a formulation using a controlled lubricant level of 120 weight percent lubricant with respect to the particulate to control porosity (sample 2A, Table 1). Pore size measurements were made with a Coulter Porometer as described in the examples. The smallest pores present were at least 0.2 micrometer and the largest were less than 1.7 micrometers in diameter. The mean pore size was 0.5 micrometer.

Figure 3:
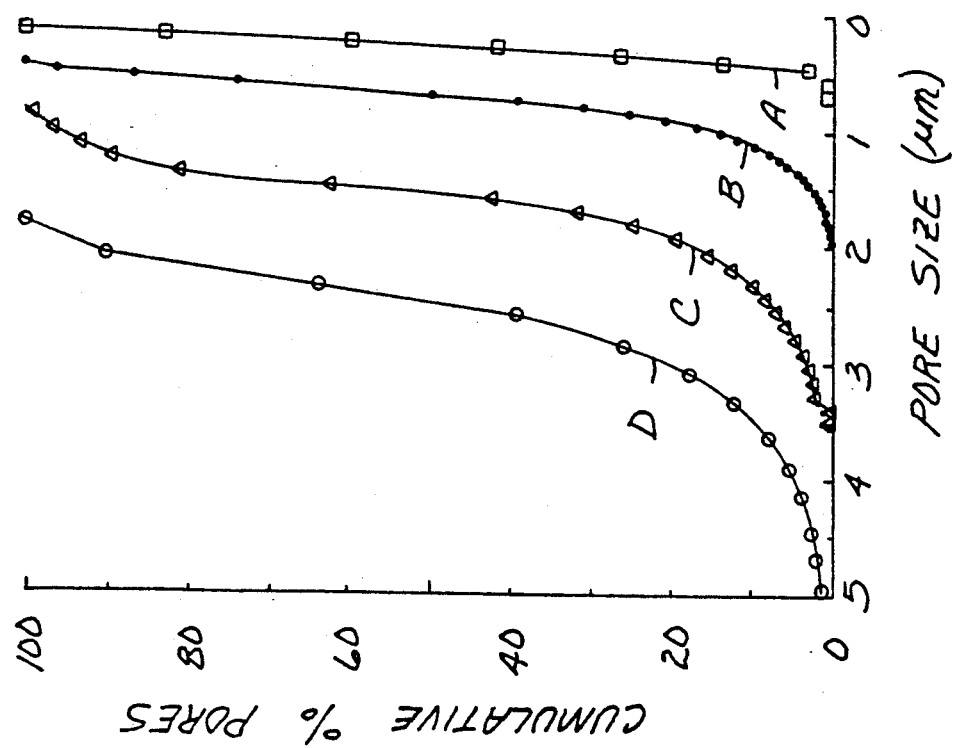
FIG. 3 is a plot of cumulative percent pores versus pore size for a series of composite articles of the invention prepared by controlling the quantities of lubricant in the formulations.

FIG. 3 is a graph which illustrates cumulative percent pore sizes as measured by the Coulter Porometer for controlled levels of process lubricant with respect to particulate [105 wt. percent (A), 135 wt percent (B), 160 wt. percent (C), 200 wt. percent (D)] and shows that the level of lubricant controls porosity (mean pore size) and void volume of the composite article. Data shown are from samples 1A, 3A, 1C, and 3C prepared as described in Example 1. Porosity (mean pore size and void volume) controls the solvent migration rate in planar chromatography and flow rates in the filtration/extraction mode of operation.

Figure 4:
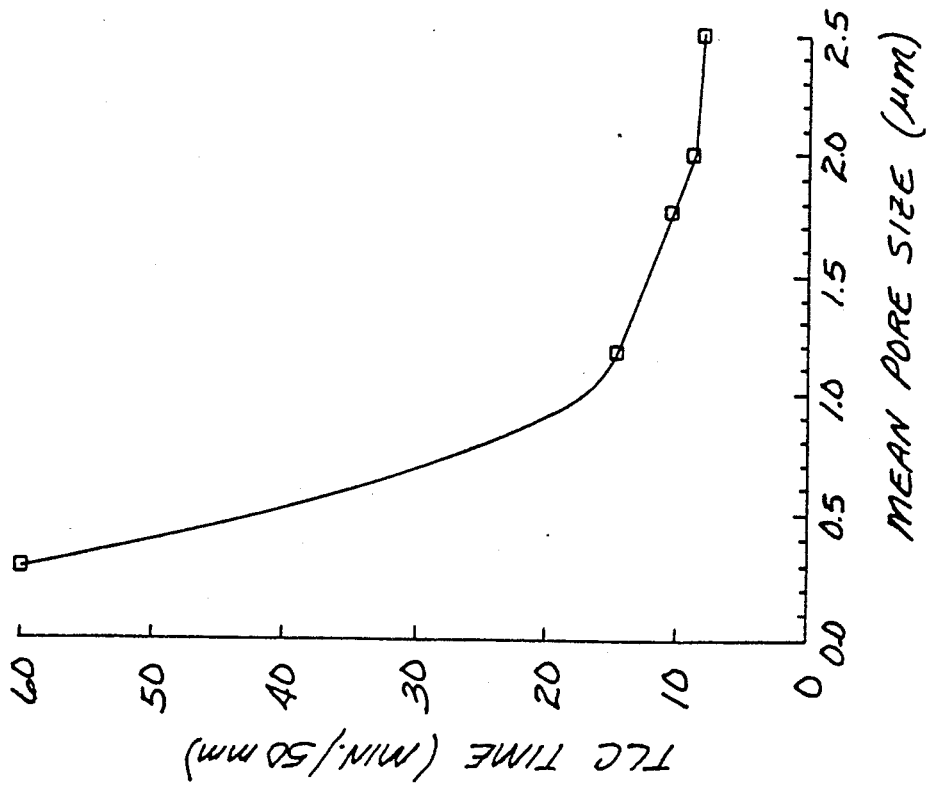
FIG. 4 is a plot of thin layer chromatography (TLC) solvent migration times as a result of different article mean porosities which were obtained using varying levels of lubricant during preparation of the article.

FIG. 4 is a graph which shows the effect the level of process lubricant (from Table 3) has on the solvent migration rate or time it takes to advance the solvent front 50 mm from the starting point in planar (TLC) chromatography. The particulate used was silica (mean size 8 micrometer) and the solvent mixture used was 0.5 volume percent methanol in dichloromethane. This particulate has a lubricant sorptive capacity approximately 75 percent of of particle weight. Solvent migration rates (minutes for 50 mm solvent migration) for the chromatographic article were:

| Migration rate (min. 50 mm migration) | Wt. % lubricant |
|---|---|
| 8.3–14.5 (preferred) | 140–200 |
| 8.3–10.5 (more preferred) | 160–200 |
| 8.3–8.8 (most preferred) | 180–200 |

If the lubricant level during processing is too low, solvent migration time is too long and the resulting article has little practical utility as a chromatographic medium. Levels of lubricant used during processing which give solvent migration times to the 50 mm distance in less than 12 minutes are most preferred which correlates with approximately 160 weight percent lubricant compared to particulate and a mean pore size of 1.8.

Figure 5:
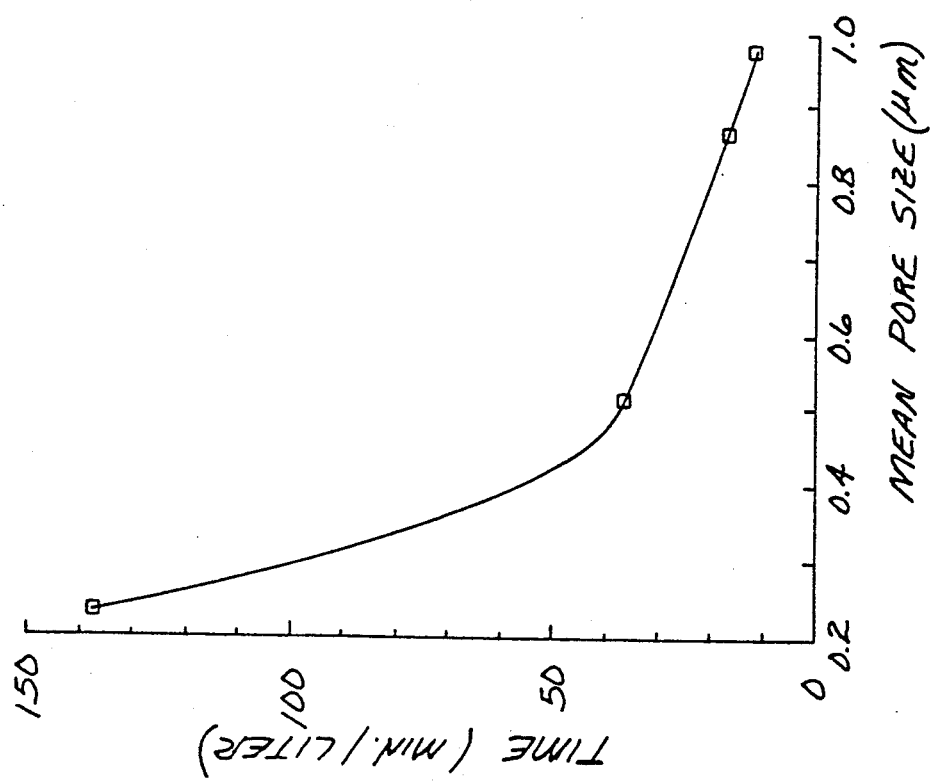
FIG. 5 is a plot of liquid filtration times for composites as a result of different composite mean porosities obtained because of various levels of lubricant used in preparation of the composite.

FIG. 5 is a graph which illustrates the effect process lubricant levels have on the flow through filtration times (47 mm diameter reverse phase disk) for one liter reagent water samples (samples 2A, 3A, 4A, 5C). The particulate used was $C_8$-derivatized silica. This graph is typical of those obtainable using non-swelling particulate, e.g., silica, derivatized silica, zirconia, coated zirconia such as polybutadiene-coated zirconia, crosslinked resin particulate such as XAD TM (Rohm and Haas, Philadelphia, Pa.), Tenax TM (Supelco, Bellefonte, Pa.), and nylon. Pore sizes for 0.5 mm thick disks containing $C_8$-derivatized silica in a flow through mode as a function of weight percent lubricant (with respect to particulate) were:

| Pore size (micrometers) | Wt. percent process lubricant |
| --- | --- |
| 0.5–2.5 (preferred) | 120–200 |
| 0.5–1.7 (more preferred) | 120–160 |
| 0.7–1.5 (most preferred) | 130–150 |

Flow times are directly dependent on the porosity of the article, which is dependent on the level of process lubricant. Flow through times of less than 30 minutes per liter are most desirable which correlates with approximately 120 wt. percent lubricant to solid particulate and a mean pore size of 0.51 micrometers. Article thicknesses in the range of 0.1 mm to 10 mm are most useful.

DETAILED DESCRIPTION OF PREFERRED EMBODIMENTS

Composite PTFE articles of the present invention have void volume in the range of 30 to 80 percent. This percent void volume can be achieved by using lubricant at least 3 and up to 200 weight percent in excess of that required to exceed the lubricant sorptive capacity of the particles. Preferred mean pore sizes for separation science applications are in the range of 0.3 to 5.0 micrometers and preferably with 90 percent of pores being less than 3.6 micrometers in size, 80 percent of pores being less than 3.2 micrometers in size, and 50 percent of pores being less than 2.5 micrometers in size. More preferably, mean pore sizes are in the range of 0.5 to 5.0 micrometers, and most preferably in the range of 0.4 to 5.0 micrometers. Preferred percent void volume is in the range of 40 to 70 percent, more preferably in the range of 50 to 65 percent, and most preferably 55 to 60 percent.

The preferred ratio of non-swellable sorptive particles to PTFE is in the range of 20:1 to 1:2 by weight, more preferably 19:1 to 1:1 by weight.

Particulate material (which can be one material or a combination of materials) useful in the present invention is substantially insoluble in water or the elution solvent. Not more than 1.0 gram of particulate will dissolve in 100 gram of aqueous media or elution solvent into which particulate is mixed at 20° C. The particulate material can be at least one of an organic compound, a polymer, or an inorganic oxide such as silica, alumina, titania, zirconia, and other ceramics, and combinations thereof, or it can be ion exchange or chelating particles or mixtures thereof, or it can be carbon. Preferred particulate materials are silica and zirconia, with silica being particularly preferred because of the ease in bonding a variety of hydrophobic and other functional coatings onto its surface and because of commercial availability. Particulates such as silica and other inorganic oxides are commercially available, for example, from Aldrich Chemical Co., Milwaukee, Wis. Zirconia is available from Z. Tech Corporation, Bow, N.H.

Suitable particulate material, also referred to as particles for purposes of this invention, includes any particle with inherent sorptive properties or those which can be coated with substantially insoluble sorptive material or the surface, external and/or internal, of which can be derivatized to provide a coating of substantially insoluble, sorptive material. Preferred supports for such coatings include inorganic oxide particles, most preferably silica particles.

The insoluble, sorptive coatings generally have a thickness in the range of one molecular monolayer to about 1 micrometer Such particles having coated surfaces are well known in the art, see, for example, Snyder and Kirkland, "Introduction to Modern Liquid Chromatography", 2d Ed., John Wiley & Sons, Inc. (1979) and H. Figge et al., "Journal of Chromatography" 351 (1986) 393–408. The coatings can be mechanically applied by in-situ crosslinking of polymers or the coatings can be functional groups covalently bonded to the surface of the organic or inorganic particles. Coatings which can be applied to silica particulate can be non-swellable polymers such as crosslinked silicones, polybutadienes, etc., or covalently bonded organic groups such as aliphatic groups of varying chain length (e.g., $C_2H_5$, $C_4H_9$, $C_8H_{17}$, and $C_{18}H_{37}$) and aliphatic and aromatic groups containing amine, nitrile, hydroxyl, chiral, and other functionalities which alter the sorptive character of the coating. Many such coated particles are commercially available (e.g., $C_{18}$ bonded phase silica, Alltech, Deerfield, Ill.).

When coated particulate are used, silica, or other support particle, can act primarily as a carrier or substrate for organic coatings and coated particles are generally non-swellable even when thin layers of swellable coatings are used. Composition of the coatings provides variations in chemical selectivity and polarity influencing separations and performance as recognized by those skilled in the art.

The particulate material may have a regular shape (such as spherical or cubic) or an irregular shape. Particulate material which has been found useful in the invention has an apparent size within the range of 0.1 to about 200 micrometers, preferably in the range of 1.0 to 100.0 micrometers, more preferably in the range of 5.0 to 40 micrometers. It has been found advantageous in some instances to employ particulate materials in two or more particle size ranges falling within the broad range. As an example, particles having an average size in the range of 0.1–100.0 micrometers having chromatographic activity may be employed in combination with particles having an average size in the range 0.1 to 250 micrometers acting as a property modifier. Such modifiers can alter the color, hydrophobicity, wettability, phosphorescent, fluorescent properties, and the like, of the composite article. Some particle size reduction may take place during the high shear mixing and the calendering operations, depending upon the friability of the particulate material. While the particulate material initially may be rather large, it may ultimately be reduced to a finer size in the final product with no adverse effects.

Particles useful in the present invention have water sorptive capacity less than 10% by weight, preferably less than 1% by weight. As noted above, particles which undergo dimensional changes due to water swellability are less desirable. In view of the teachings of U.S. Pat. Nos. 4,565,663 and 4,460,642 it is surprising that hydrophobic particles and other non-swellable particles enmeshed in PTFE provide superior chromatographic articles compared to water-swellable hydrophilic particles enmeshed in PTFE.

In contrast to the teachings of the background art, surprisingly and unexpectedly we found that when we altered and exceeded the quantity of lubricant normally used in formulations to facilitate introduction of additive and adjuvant particles within a PTFE matrix to provide a resultant PTFE-containing composite article, we were able to control porosity and void volume and achieve desirable results. This means for achieving increased and controlled porosity in a PTFE composite without use of contaminating extractable/leachable fillers is vital to the performance of the composite in the separation science field.

As described in the method of U.S. Pat. No. 4,153,661, the active sorbent particles useful in the present invention can be pre-mixed with a property modifier. Representative non-swellable property modifiers (some of which may be soluble in water) can be coated particles, ion exchange particles, calcium carbonate, ammonium carbonate, kaolin, sugar, polyethylene, polypropylene, polyester, polyamide, polyurethane, polycarbonate, zeolites, chitin, vermiculite, clay, ceramics, chelating particles, and the like. These property modifier materials can be present in an amount in the range of more than 0 up to 28.99 parts per part of PTFE, preferably more than 0 up to 9.00 parts per part of PTFE, provided that the sorptive non-swellable particles plus property modifiers do not exceed 29 parts particulate to 1 part PTFE. These ranges are desirable to achieve a preferred tensile strength of at least 0.01 MegaPascal (MPa) in the composite structure.

Other non water-swellable property modifiers may be advantageously added to a mixture of the PTFE aqueous dispersion and the primary particulate material to provide further improvement in or modification of the composite articles of the invention. For example, modifier particulate can include chromatographically inactive materials such as low surface area glass beads which can act to assist in the fibrillation process by acting as a processing aid.

A limited amount of water-swellable property modifiers (i.e., up to 30 weight percent, preferably less than 25 weight percent, more preferably less than 10 weight percent, and most preferably less than 1 weight percent, of total particulate) can be useful. Representative swellable property modifiers include starch, chitosan, modified starches such as Sephadex TM and Sepharose TM (Pharmacia, Sweden), agarose, polymethacrylates, certain styrene-divinylbenzene copolymers, polyacrylamides, cellulosics such as cellulose fibers, and coated particles (e.g., silica coated with a polyacrylamide). Water-swellable materials may be used as a thin coating on non-swellable particulate with the net result being a net non-swellable particulate for chromatographic purposes.

When the particulate is hydrophobic, the preferred method of manufacture of the article of this invention utilizes an emulsion of PTFE with a property modifier added to enhance the hydrophobic particle surface/water interaction and to allow rapid wetting of the surface of the hydrophobic particulate. Preferred modifiers for this purpose are organic compounds such as alcohols, amines, acids, etc. with the preferred compounds being alcohols due to their efficacious removability, e.g., by solvent extraction or by drying after fabrication of the article.

It is desirable from a surface energy standpoint to minimize the PTFE level and at times to alter the level of the active particulate. Coloring or fluorescent particulates can be added at low levels (up to 10 weight percent of particulate) to aid in visualizing sample components separated or to be separated. Chemically active particulates which indicate chemical properties and pH of a mixture's resultant separated component bands, can be useful for diagnostic purposes.

The process of the present invention represents an improvement over prior art processes. Specifically, the PTFE composite article of the invention is prepared by mixing the particulate or combination of particulates employed, PTFE and lubricant, until a uniform mixture is obtained. PTFE and lubricant can be added as a PTFE resin emulsion which is commercially available from DuPont. It has been found that to optimize separation techniques in the resultant article, the amount of lubricant in the mixture, or subsequently added lubricant, i.e., water or water based solvent or organic solvent, should be present in an amount sufficient to exceed the lubricant sorptive capacity of the particles preferably by at least 3 weight percent up to 200 weight percent, more preferably in an amount to exceed the lubricant sorptive capacity of the particles in the range of at least 5 to 200 weight percent, even more preferably at least 25 to 200 weight percent, and most preferably at least 40 and up to 150 weight percent. These ranges can be optimized for obtaining the desired mean pore sizes for different types of particles and for the different types of separations to be performed. For a lubricant/$C_8$ derivatized silica system, lubricant should be present in the range of 103 to 200 percent by weight with respect to solid particulate in the PTFE composite article, preferably 105 to 200, more preferably 110 to 180 percent by weight, and most preferably 115 to 175 weight percent.

Because various particulate differ in lubricant sorptive capacity, optimum lubricant levels will depend upon the particles selected. For a functionalized or derivatized organic resin system, such as a sulfonated cation exchange resin, the optimum or most preferred lubricant range is 150 to 200 weight percent of particle weight.

Lubricants useful in the present invention process can be water; water-based solvent such as water-organic solvent, e.g., water/alcohol in any proportion, preferably in the range of 4:1 to 1:4, more preferably in the ratio of 1:1, wherein the alcohol can be any alcohol that can be conveniently removed by washing or drying, preferably the alcohol is a $C_1$ to $C_5$ alkanol; or other organic solvents such as ketones, esters, and ethers which can be conveniently removed, for example, by washing or drying.

Blending takes place along with the controlled amount of lubricant which exceeds the lubricant sorptive capacity of the particles by at least 3 percent by weight to generate the desired porosity level of the resultant article. The aqueous PTFE dispersion can then be blended with the particulate mixture (which can include property modifiers and processing aids) to form a mass having a soft putty-like or dough-like consistency. Lubricant sorptive capacity of the solids of the mixture is noted to have been exceeded by at least the desired amount when moderate amounts of lubricant can no longer be incorporated into the mass without separation. This condition should be maintained throughout the entire mixing operation. The soft putty-like mass is then subjected to intensive mixing at a temperature up to 90° C., preferably in the range of 0° C. to 90° C., more preferably in the range of 20° C. to 60° C. for a time sufficient to cause initial fibrillation of the PTFE particles. Minimizing the mixing at the specified temperature is essential in obtaining chromatographic transport properties (e.g., flow-through or wicking).

Mixing times of the formulation will typically vary from 0.2 to 2 minutes to obtain the necessary initial fibrillation of the PTFE particles. Initial mixing causes partial disoriented fibrillation of a substantial portion of the PTFE particles. Initial fibrillation will be noted to be at an optimum within about 90 seconds after the point when all components have been fully incorporated together into a soft putty-like (dough like) consistency. Mixing short of or beyond this point may produce a composite sheet of inferior chromatographic properties.

Devices employed for obtaining the necessary intensive mixing are commercially available intensive mixing devices which are sometimes referred to as internal mixers, kneading mixers, double-blade batch mixers as well as intensive mixers and twin screw extruder compounding mixers. The most popular mixer of this type is the sigma-blade or sigma-arm mixer. Some commercially available mixers of this type are those sold under the common designations Banbury TM mixer, Mogul TM mixer, C. W. Brabender Prep TM mixer and C. W. Brabender TM sigma blade mixer. Other suitable intensive mixing devices may also be used.

The soft putty-like mass is then transferred to a calendering device. The mass is subjected to biaxially calendering between gaps in calendering rolls maintained at a temperature up to 125° C., preferably in the range of 0 to 100° C., more preferably in the range of 20 to 60° C. to cause additional fibrillation of said PTFE particles to form a self-supporting sheet, while closing the gap between the calendering rolls with each successive calendering operation, for a time sufficient to produce a tear-resistant sheet having a preferred tensile strength of at least 0.01 megapascal, more preferably at least 0.05 megapascal; and optionally drying the resultant sheet to remove lubricant to provide a composite sheet comprising a network of interlaced microfibrous PTFE forming a fibril matrix having enmeshed therein said sorptive particles. The lubricant level of the mass is maintained at least at a level of exceeding the absorptive capacity of the solids by at least 3 percent by weight, until sufficient fibrillation occurs and to produce porosity or void volume of at least 30% and preferably 40 to 70% of total volume. The preferred amount of lubricant is determined by measuring the pore size of the article using a Coulter Porometer as described in the Examples below. Increased lubricant results in increased pore size and increased total pore volume.

The PTFE aqueous dispersion employed in producing the PTFE composite sheets and other articles of this invention is a milky-white aqueous suspension of minute PTFE particles. Typically, the PTFE aqueous dispersion will contain about 30% to about 70% by weight solids, the major portion of such solids being PTFE particles having a particle size in the range of about 0.05 to about 1.5 micrometers. Commercially available PTFE aqueous dispersion may contain other ingredients, for example, surfactant materials and stabilizers which promote continued suspension of the PTFE particles. In some applications it is advantageous to remove the surfactant by extraction or by choosing a PTFE emulsion which is free of surfactant.

Such PTFE aqueous dispersions are presently commercially available from E. I. Dupont de Nemours, Wilmington, Del.), for example, under the trade names Teflon TM 30, Teflon TM 30B, or Teflon TM 42 Teflon TM 30 and Teflon TM 30B contain about 59% to about 61% solids by weight which are for the most part 0.05 to 0.5 micrometer PTFE particles and from about 5.5% to about 6.5% by weight (based on weight of PTFE resin) of non-ionic wetting agent, typically octylphenol polyoxyethylene or nonylphenol polyoxyethylene. Teflon TM 42 contains about 32 to 35% by weight solids and no wetting agent but has a surface layer of organic solvent to prevent evaporation. It is generally desirable to remove, by organic solvent extraction, any residual surfactant or wetting agent after formation of the article to avert potential interference in separatory and chromatographic applications.

The present invention provides a novel article having a composite structure and method therefor, the composite structure preferably being a uniformly porous, composite sheet comprised of non-water swellable sorptive particles distributed uniformly throughout a matrix formed of intertangled, PTFE fibrils. In such a structure, almost all of the particles are separated one from another and each is isolated and not adhered one to another, or to a cage-like matrix, that restrains the particle on all sides by a fibrillated mesh of PTFE microfibers as shown in FIG. 1. The preferred novel sheet of this invention has a thickness in the range of 100 to 10,000 micrometers, preferably 125 to 5,000 micrometers, more preferably 150 to 2,500 micrometers, and has a tensile strength of at least 0.01 MPa and even as high as 5.0 MPa.

The article is substantially uniformly porous, making it suited for use as a chromatographic composite article which can be used as a single self-supporting sheet or a combination of sheets to form a laminate/stack or as a composite adhered to an inorganic support such as metal or glass, or to an organic support such as paper or polymers. The laminate/stack can contain layers of composites with different porosities. Controlled porosity is a necessary characteristic of the composite article to achieve useful chromatographic performance.

In a first mode, PTFE-particulate technology can be useful wherein the composite article of the invention is used for pre-concentration and isolation of certain materials for further analysis by a variety of analytical techniques such as gas or liquid chromatography. In this flow through mode, which is well known in the membrane filtration and solid phase extraction art, solvent and sample flow are introduced at an angle of 90 degrees to the surface of the sheet. This is a conventional configuration and the separation path length is equal to the thickness of the sheet and the tortuosity of the matrix. The path length can be increased by stacking additional layers but the individual layers may not be intimately bound together since the calendering operation may be limited to a specific thickness. This mode is effective for one step or multiple step adsorption-desorption separations. This mode is also effective using reactive particulate such as ion exchange materials, chelating materials, or sorptive particulate in the normal/reverse phase modes or combinations thereof.

Utility of this membrane mode can be enhanced by inclusion of many other reactive particulates to carry out chemical and physical separations to be described. The article strongly sorbs the component of interest in a mixture onto the active particulate in the composite and undesirable components are either not sorbed (pass through the membrane) or washed out (eluted) with a first solvent. A second solvent, with greater affinity for the isolated component than exhibited by the particulate, is then used to displace the desired component from the particulate allowing the component to be recovered in a more concentrated and purified form.

In a second mode, the flow is parallel to the surface or zero degrees into the edge or through the lengthwise dimension of the sheet. Path length for the separation can be selected from the dimensions of the material used and flow is dependent on the ability to transport solvent by capillary action or with forced flow (externally applied pressure) conditions. Multiple, continuous sorption and desorption steps are needed to obtain high resolution chromatographic separations and require a minimum path length which is not practical to obtain by stacking disks of the composite in column configuration. In this mode, the composite is useful to obtain analytical and preparative separations which are analogous to TLC or planar chromatography (PC) where solvents and sample components are normally transported through the media by capillary action but forced flow conditions can also be utilized.

It is believed that solvent or eluant migration rates through the composite article are dependent on the porosity and are also influenced by the net surface energies of the PTFE fibrils, the chromatographically active particulate such as silica, and any modifier particulate. Small amounts of PTFE appear to dominate the net surface energy contribution to the eluant migration rates. This may be due to the construction and method of making the article wherein the active silica particles appear not to touch each other and solvent eluant mobility is dependent on the low surface energy of PTFE fibrils. In a preferred mode, using silica as particulate, several experiments were performed varying the ratios from 95/5 to 80/20 (silica/PTFE) and we found that the higher the silica content, the faster the rate of solvent and component migration. This appears to be a function of the net surface energy of the composite sheet material.

Net surface energy of the composite article is the net weighted average of the surface energies of PTFE matrix ($E_{PTFE}$), the active sorptive particulate ($E_{part}$), and modifying particulate ($E_{mod}$). It is desirable that the net surface energy be in the range of 20 to 300 milliNewtons per meter, preferably 50 to 300 mN/M. This provides optimization of surface energy for solvent and solute transport. The net surface energy of a particulate is comprised of polar and non-polar forces. Polarity is equal to the ratio of polar surface energy to the total surface energy. For example, polarity of PTFE, Nylon 66, and silica are calculated from surface tension data to be 0.10, 0.21, and 0.38, respectively.

Composite articles of the present invention have high capacity for sample loading and can be very useful for preparatory or process scale chromotography. Migration rate of an eluant (solvent) can be increased dramatically using radial chromatography wherein centrifical force is utilized to force the solvent through the porous chromatographic article. This process is well known in the art. In the background art, higher amounts of "glue" or binder are normally needed to hold the chromatographic materials, such as silica to the conventional spinning glass plate, whereas in articles of the present invention, the porous fibrillated PTFE composite needs no binder or supporting plate. In the background art, particulates successfully adhered to glass plates have been limited to silica and alumina. The present invention has a great advantage in that virtually any organic or inorganic particulate can be entrapped in the PTFE fibrillated matrix for many chromatographic applications. No binder is required. Absence of any binder is of particular significance in reverse phase systems with non-swellable hydrophobic particulate.

Composite chromatographic articles of this invention can be of a variety of sizes and shapes. Preferably the articles can be sheet-like materials which, for example, can be in disk or in strip form. Coating the non-swellable particulate with very thin (mono-layer) materials or thicker materials provided by in-situ crosslinking of polymers or covalently bonding functional molecules on the surface of the particulate allows for optimization of both chromatographic selectivity and separation efficiency.

Composite articles of this invention have utility in a wide variety of physical size and chemical sorptive separations wherein choice of the particulate material is useful for size controlled filtration or molecular range steric exclusion. These articles have utility for simple one step or multiple step adsorption-desorption separations of specific components, for immobilization of reactive particulate to perform chemical or diagnostic biochemical reactions, for ion-exchange conversion and isolation of cations and anions, for purification of materials, and for chromatographic separations and analyses in both passive and forced flow modes, for hydrophobic reverse phase and normal phase chromatography. In all of the examples described, controlled porosity is a critical factor in performance of articles in the chromatographic mode.

In particular, embodiments of the articles of the invention can be useful in environmental applications in removing or isolating pollutants, including toxins and pesticides, etc., from air, water, soil, food, and beverages. In addition, articles of the invention can be useful in clinical application in isolating and concentrating drugs, metabolites, etc., from biological fluids.

Objects and advantages of this invention are further illustrated by the following examples, but the particular materials and amounts thereof recited in these examples, as well as other conditions and details, should not be construed to unduly limit this invention. In the Examples, in all cases of composites prepared within the invention lubricant was added in an amount to exceed the sorptive capacities of the particles in the range of 3 to 200 weight percent. Parts and percentages in the Examples are by weight unless otherwise indicated.

EXAMPLES

Example 1

In this example, a series of composites were prepared using an improvement in the work intensive procedure as described in Example 2, U.S. Pat. No. 4,810,381. In this case, in addition, we carefully controlled the level of lubricant (1 part water/1 part isopropyl alcohol), to produce articles, each having different porosities.

For sample 1A, ten grams of $C_8$ bonded silica (Analytichem Int., Harbor City, Calif.) was placed in a 100 ml beaker. This particle has a lubricant sorptive capacity approximately 75 percent of particle weight. 1.6 grams of polytetrafluoroethylene (PTFE) resin emulsion (Teflon TM 30B, E. I. Dupont, Inc., Wilmington, Del.) was added stepwise in three portions with intermittent vigorous stirring This provided a $C_8$ bonded silica to PTFE ratio of 90/10. The temperature can be up to 90° C., preferably in the range of 0° to 90° C., more preferably about 23° C. 10.5 grams of lubricant was added stepwise in three portions with intermittent vigorous stirring. After these ingredients had been thoroughly mixed, a semi-coherent material was formed with enough physical integrity to allow the entire contents of the beaker to be removed as a single mass. The above mass was passed between two rollers kept at 50° C. It is also possible to maintain the rollers up to 125° C., preferably 0° to 100° C., more preferably 20° to 60° C., and spaced about 0.5 cm apart to give a strip of cohesive material. The resulting strip was folded to three thicknesses and then passed through the rollers after a 90 degree rotation from the previous pass. The cyclic process of folding and re-rolling in a direction 90° from the direction of the previous pass was repeated multiple times to give a tough, strong, flat piece of material. The material was then calendered along the long axis via a series of roller passes with roller spacing adjusted to successively smaller distances apart to give a continuous ribbon. The ribbon was folded to give a multi-layer piece which was then calendered as before along the axis 90° from the calendering direction used previously.

The calendered sheet of material was then allowed to dry in air for 48 hours. The procedure described in Example 1 was repeated with increasing amounts of lubricant (samples 2A, 3A, 4A) and data on the resulting composites are shown in Table 1. Results obtained definitely showed that porosity could be produced in a predictable manner without use of extractable or leachable adjuvants as taught in the background art. The data illustrate the minimum, mean, and maximum pore size distributions, as measured by the Coulter Porometer, (Coulter Electronics Inc., Edison N.J.) for different levels of lubricant in the formulation. FIG. 2 illustrates pore size distribution obtained on sample No. 2A using the Coulter Porometer.

TABLE 1

| | Lubricant Effect on Pore Size Distribution | | | |
|---|---|---|---|---|
| | | Sample Pore Size (μm) | | |
| Sample No. | % Lubricant* | Minimum | Mean | Maximum |
| 1A | 105 | 0.115 | 0.237 | 0.859 |
| 2A | 120 | 0.244 | 0.511 | 1.659 |
| 3A | 135 | 0.470 | 0.864 | 2.680 |
| 4A | 150 | 0.524 | 0.972 | 2.938 |

*Note that water/alcohol lubricant levels listed in Table 1 refer to the weight percent ratios of lubricant to solid particulate.

The data of Table 1 show that increasing weight percent lubricant provides an article with larger minimum, mean, and maximum pore sizes. Sample No. 3A was shown to be useful to extract therapeutic drugs and their metabolites from blood serum in greater than 90 percent recovery.

Example 2

This example illustrates the effect which celluose, used as a hydrophilic modifier particulate mixed with the silica, has on the pore size of a resultant prepared PTFE composite chromatographic article. These composites were prepared with different levels of lubricant (see Table 2, below) to control porosity as described in Example 1 above with the exception that 0.35 percent by weight 40 micrometer diameter cellulose fibers (Sigma Cel TM, Sigma Chemical Co., St. Louis, Mo.) were added to the silica particulate in the process. Results are given in Table 2.

A comparison of the data between Tables 1 and 2 illustrates that increased porosity results from a small (0.35%) amount of the cellulose modifier particulate which is not leached or extracted out of the composite article.

In contrast, the background art taught use of removal (be extraction/leaching) particles such as salt, extractable organics, and the like, to generate a degree of porosity in the final product. The cellulose particles were not extracted and we believe the induced porosity was due to the hydrophilicity and swellability of cellulose particles to form micro channels in the composite matrix. Furthermore, in the field of separation science, and especially in chromatography, it is very important to avoid use of foreign extractables, which usually leave residues which interfere in trace analysis. Moreover, those skilled in the art realize that it is virtually impossible to completely remove traces of many extractable additives which interfere with subsequent analytical procedures at less than 1 part per trillion level.

TABLE 2

| | Lubricant Effect on Pore Size Distribution (0.35% Cellulose Modifier) | | | |
|---|---|---|---|---|
| | | Sample Pore Size (μm) | | |
| Sample No. | % Lubricant* | Minimum | Mean | Maximum |
| 1B | 105 | 0.214 | 0.392 | 1.299 |
| 2B | 120 | 0.458 | 0.907 | 2.614 |
| 3B | 135 | 0.582 | 1.089 | 3.122 |
| 4B | 150 | 0.653 | 1.257 | 3.618 |

*Note that water/alcohol lubricant levels listed in Table 2 refer to the weight percent ratios of lubricant to solid particulate.

The data of Table 2 show that increasing percent lubricant provides an article with larger minimum, mean, and maximum pore sizes. In addition, the data show increase in pore size resulting from use of cellulose as a property modifier.

Example 3

Example 3 illustrates the effect of lubricant level on pore size, density, TLC migration rate (including a comparative study), and filtration mode flow-through rate, all of which are important to chromatographic use of the article.

Table 3 shows data obtained for five samples made at different levels of process lubricant (water/alcohol in a ratio of 1 to 1) using ingredients and procedures as described in Example 1. Sample 5C was prepared by the dry or lubricant-free process (U.S. Pat. No. 3,864,124).

TABLE 3

| | Lubricant Level Effect on Sheet Characteristics | | | | |
|---|---|---|---|---|---|
| Sample No. | % Lubricant* | Pore Size (Mean μm) | Density (g/cc) | TLC (min/ 50 mm) | Filtration Time (min/liter) |
| 1C | 200 | 2.50 | 0.455 | 8.32 | 1.35 |
| 2C | 180 | 2.00 | 0.473 | 8.83 | 1.87 |
| 3C | 160 | 1.76 | 0.486 | 10.50 | 3.25 |
| 4C | 140 | 1.17 | 0.514 | 14.47 | 6.73 |

TABLE 3-continued

| | Lubricant Level Effect on Sheet Characteristics | | | |
|---|---|---|---|---|
| Sample No. | % Lubricant* | Pore Size (Mean μm) | Density (g/cc) | TLC (min/ 50 mm) | Filtration Time (min/liter) |
| 5C** | 0 | 0.29 | — | 60.0 | 68.6 |

**Comparative
*Note that water/alcohol lubricant levels listed in Table 3 refer to the weight percent ratios of lubricant to solid particulate.

As in Tables 1 and 2, Table 3 shows the relationship between mean pore size and lubricant level. FIG. 3 shows plots of cumulative number pore size data. Each of the four curves represents data from a different lubricant level, as detailed above for samples 1C-4C. The relationship between lubricant level and pore size distribution was clearly demonstrated. The data also show density is related to porosity/void volume.

The data of Table 3 also show the relationship between mean pore size, TLC solvent (0.5 vol. percent methanol in dichloromethane) migration velocity, and lubricant level. TLC times under 10 minutes for 50 millimeters (mm) travel are most preferable. Sample 5C, prepared by the dry process, gave unacceptably long solvent migration times which is a direct consequence of the lack of adequate porosity. This is understandable since the object of certain background art was to prepare a pore-free article and a lubricant-free process was used. This background art composite was not usable as a chromatographic material since the porosity was so low as to prevent acceptable solvent flow through the sorptive media. In fact, the reference (U.S. Pat. No. 3,864,124, column 17, lines 54-56) teaches "A fluid is passed over the unsintered composition to selectively desorb and separate the chemical compounds."

FIG. 4 (data of Table 3) illustrates the dependence of TLC solvent velocity on porosity as obtained in this composite article by controlling the ratio of lubricant to solid particulate. Times less then 30 minutes, preferably less then 15 minutes are most desirable to advance the solvent front to 50 mm from the starting point. Those skilled in the art will recognize that resolution/separation of the component mixture is dependent on optimal solvent velocity.

Table 3 also shows the data obtained for the composite sheet in vacuum assisted filtration or flow-through mode for one liter water samples. The data are listed for the flow times in minutes per liter and clearly show the role that the process lubricant plays in filtration rates. Sample 5C, made by the lubricant-free comparative process, is not acceptable since the lack of adequate porosity results in unacceptably long periods of time to filter a standard one liter water sample.

Data of FIG. 5 show the effect of the mean pore size on flow-through times as measured in the filtration or extraction mode of operation. A 47 mm by 0.5 mm disk was placed in a Millipore TM filtration apparatus (Millipore Corp., Bedford, Mass.). A vacuum of 90 kPa (26 inches of mercury) was applied and the resultant flow-through times are listed for 1 liter quantities of water containing 0.5 percent methanol. Mean pore sizes in the 0.5 to 5.0 micrometer range are the most useful range for this invention. Mean pore sizes from 0.5 to 1.5 micrometer are the most preferred. Ability to control pore size is of great utility in the filtration/separation mode and also the sorptive properties of the entrapped particulate permit sorptive separations or isolations at the molecular level.

Table 4, below, shows data obtained in a comparative study of chromatographic solvent migration rates using 1) an article prepared essentially as described in U.S. Pat. No. 4,810,381, Example 2, sample 10A (PTFE/silica 90/10), and 2) the article of the instant invention as described in Example 3, Sample 2C (PTFE/silica 90/10). Each of the articles was 500 micrometers (20 mil) thick. The times of solvent flow (0.5 percent methanol in methylene chloride) are given in Table 4.

TABLE 4

| | Solvent Migration Rate in Chromatographic Article | | |
|---|---|---|---|
| Data point | mm Travelled | Comparative 10A (min) | Invention 20 (min) |
| 1 | 0.0 | 0.00 | 0.00 |
| 2 | 5.0 | 0.48 | 0.22 |
| 3 | 10.0 | 1.33 | 0.68 |
| 4 | 15.0 | 2.68 | 1.27 |
| 5 | 20.0 | 4.45 | 2.02 |
| 6 | 25.0 | 6.62 | 3.02 |
| 7 | 30.0 | 9.13 | 4.10 |
| 8 | 35.0 | 12.27 | 5.37 |
| 9 | 40.0 | 15.67 | 6.97 |
| 10 | 45.0 | 19.93 | 8.80 |

The data of Table 4 show that times of solvent flow were more than twice as fast when the instant invention chromatographic article was compared with that of U.S. Pat. No. 4,810,381, Example 2.

Clearly, controlled amounts of lubricant water or water-alcohol mixture used in the formulation during the process of making the composite has a direct effect on the resultant pore size/void volume of the final product. Apparently, the lubricant, being non-compressible during the work intensive composite manufacturing process, accounts for porosity and ability to control pore size/void volume in articles of the present invention.

Example 4

This example illustrates a method of using the composite controlled pore article in a flow-through sorption mode. Controlled porosity is important for controlling flow rate of aqueous samples containing hydrophobic organic materials though the composite article in sheet form. Optimum flow rate occurs when the flow rate is slow enough for quantitative capture of hydrophobic compounds from water, but fast enough to allow a reasonable analysis time, preferably less than 60 minutes for a one liter water sample, most preferably less than 30 minutes for a 1 liter water sample, as with sample 2A shown in Example 1.

The principle of this method is that, as the water sample passes through the composite, the hydrophobic organic species of interest are captured by the hydrophobic particulate. After the water sample has been thus processed, the species of interest are removed from the particulate by passing a small volume of a less polar solvent (which is capable of displacing and dissolving the sorbed species) through the composite. This same principle can be used in many situations where it is desired to extract hydrophobic organic species from a mostly aqueous extract hydrophobic organic species from a mostly aqueous sample, such as analysis of pollutants in water (environmental analysis) or analysis of drugs and metabolites in biological fluids (clinical analysis). This method is known to those skilled in the art as "solid phase extraction." This mode is most useful in the one step or multiple step adsorption-desorption separations described earlier.

The prior art taught solid phase extraction using particles packed in columns or cartridges to perform the capturing of organic materials (isolation step). Particle-packed columns or cartridges limits control of porosity, since porosity and thus flow rate results mostly from the type and size of particulates. Furthermore, particle-packed columns or cartridges are subject to channeling (the opening of voids or channels through which a water sample can pass without interacting with the particulate, the result being incomplete and inefficient removal of the organic material from the sample).

In contrast, the present invention provides particulate loaded composite sheets or membranes to isolate these organic materials in water or other solvent wherein the porosity of the article can be controlled independently of particle size and type. Moreover, channeling is prevented because of the construction of the article, i.e., particulate is enmeshed in a fibrillated PTFE matrix.

Table 5, below, shows the data obtained for an application wherein environmental pollutants such as pesticides at a level of 1 part per billion (ppb) were extracted from a one liter water sample (artificially fortified with the pesticides) by passing the sample through a sheet form of the composite article of this invention containing $C_8$ derivatized silica particulate.

The composite article in this case contained 90 percent by weight $C_8$ bonded phase silica and 10 percent by weight PTFE. The composite was made by the work intensive procedure described in Example 1 with a lubricant (water/alcohol in a ratio of 1 to 1) to particulate ratio of 120 percent to give a mean pore size similar to that of sample 2A (see Table 1).

A die cut disk of the sheet material of sample 2A of Example 1, 47 mm in diameter and 0.5 mm thick was placed in the vacuum filtration assembly described above in Example 3 for the filtration/extraction steps. The disk was conditioned by a pre-wetting step with 5 ml of methanol and the liter of water was prepared by adding 5 ml of methanol. Both steps were considered necessary to wet the $C_8$ derivatized silica particulate. Pesticides were preferentially sorbed by the hydrophobic particulate and thus extracted/removed from the water sample passing through the disk. The water sample was pulled through the disk using an applied vacuum. The amounts of pesticides extracted were then identified and determined by removing them from the composite article in a very concentrated (50–100 times) and purified form by elution with an organic liquid such as ethyl acetate. The eluant was analyzed by gas chromatography to determine the amounts of pesticides recovered from the water sample. Data (see Table 5) show that the composite sheet article had a high efficiency in removing and isolating pesticides from water.

TABLE 5

Percent Recovery of Pesticides Extracted
From Surface Water at 1 ppb Level

| Pesticide | Recovery |
| --- | --- |
| Propachlor TM (Monsanto Co.) | 86 |
| Atrazine TM (Geigy Agricultural Chemicals) | 110 |
| Metribuzin TM (Chemagro Agricultural Chemicals) | 28* |
| Alachlor TM (Monsanto Co.) | 90 |

TABLE 5-continued

Percent Recovery of Pesticides Extracted
From Surface Water at 1 ppb Level

| Pesticide | Recovery |
| --- | --- |
| Cyanazine TM (Shell Chemical Co.) | 96 |
| Chlorpyrifos TM (Dow Chemical) | 86 |

*pesticide is suspected to degrade which accounts for low recoveries

The data of Table 5 show that the composite article of this invention can be used instead of solid phase extraction cartridges and columns to isolate pollutants from water, air, soil, food-stuffs, beverages and the like by proper choice of the sorptive particulates enmeshed in the composite article and the proper choice of solvent to remove (elute) the pollutants.

Disks, because of their large surface area, allowed faster flow rates at the same linear velocity through a particulate article than did cartridges. As a result of a disk's simplicity, inertness, and purity of materials of construction, a minimum of interfering materials were extracted by an eluting liquid.

In some cases, pollutants were removed from the article by heating the article and thermally desorbing the pollutants of interest in subsequent analysis. Similarly, the pollutant could be removed from the composite article using extraction with a supercritical fluid, such as carbon dioxide with subsequent analysis.

Example 5

Example 5 illustrates use of polymer coated inorganic particles, in place of bonded inorganic particles, as a reverse phase material for the flow-through extraction of hydrophobic species from water. Particulate used in this Example was 20 micrometer zirconia which had been coated with 2 percent by weight polybutadiene as disclosed in U.S. Pat. No. 4,810,381, col. 4, lines 33–65. The coated particles were incorporated into the composite article using the procedure described in Example 1.

Articles containing polybutadiene coated zirconia particulate (as a filter disk) were used for removing and concentrating hydrophobic compounds, such as pollutants, from water in a method similar to that in Example 4 above. In this case, the compounds used to fortify one liter water samples were a hydrophobic dye (Disperse Red 1, Aldrich Chemical Co., Milwaukee, Wis.) and four phthalate esters (dimethyl-, diethyl-, di-n-butyl-, and di-n-octyl-), each compound at a concentration of 100 ppb (micrograms per liter). Flow times for the one liter water samples were 12 min, and elution solvents were methanol for the dye and acetonitrile for the phthalate esters (plasticizers). At this point, the eluants were brought to 10 ml in a volumetric flask and analyzed as is known to those skilled in the art by visible spectroscopy for the dye (480 nanometers) and reverse phase high performance liquid chromatography for the four phthalate esters. Analytical data are shown in Table 6, below.

TABLE 6

Recovery of Hydrophobic Compounds
From a Coated Particulate

| Compound | Recovery (percent) |
| --- | --- |
| disperse Red 1 | 98 |
| dimethyl phthalate | <1 |
| diethyl phthalate | 4 |

TABLE 6-continued

Recovery of Hydrophobic Compounds
From a Coated Particulate

| Compound | Recovery (percent) |
| --- | --- |
| di-n-butyl phthalate | 90 |
| di-n-octyl phthalate | 94 |

Data of Table 6 show that the coated particulate-containing disk is useful for the recovery of hydrophobic compounds from essentially aqueous samples. The less hydrophobic compounds, such as the dimethyl- and diethylphthalates showed much lower recoveries.

Although this disclosure has demonstrated the utility of a controlled pore article for environmental and clinical separations and purifications on an analytical scale, these applications could be scaled up to a process scale. Such applications could include treatment of air or contaminated water for removal of pollutants or therapeutic treatment of biological fluids for the purpose of removing and isolating contaminants, e.g., certain toxins, metabolites or drugs.

Example 6

Higher temperatures can be used to make the composite articles. As an example, a composite comprising PTFE and silica (90:10 percent by weight) was made at a calender roll temperature of 125° C. The article was made in accordance with the method of Example 3 but with lubricant amount at 170% of particle weight. The lubricant absorbant capacity of the silica particle mass was 140% of the particle weight. The data is given in Table 7 below and show a useful composite was obtained. The filtration data was obtained from a disk having an effective diameter of 38 mm.

TABLE 7

| Sample No. | Temperature °C. | % Lubricant | Pore size (mean μm) | TLC (min/50 mL) | Filtration (min/L) |
| --- | --- | --- | --- | --- | --- |
| 1D | 125 | 170 | 0.61 | 16.00 | 45.5 |

The data of Table 7 show that even with 170% lubricant, high temperature had the effect of reducing the mean pore size.

Example 7

The amount of PTFE in the article can be variable. For this example a composite (disk with an effective diameter of 38 mm) was produced according to the method of Example 3 but with lubricant at 3% by weight in excess of the lubricant sorptive capacity of the particulate (PTFE:silica was 80% : 20% by weight). The mean pore size of this membrane was too small to measure using the Coulter TM Porometer (i.e., less than 0.2 micrometer). The data is given in Table 8, below.

TABLE 8

| Sample | Filtration Time-Water (min/mL) | Filtration Time-Toluene (min/mL) | TLC (min/50 mm) |
| --- | --- | --- | --- |
| 80% PFTE 20% silica | 7.1 | 1.4 | 420 |

Example 8

A composite (disk with an effective diameter of 38 mm) was made from the material of Example 5 according to the method of Example 1 but with a particle (zirconia) to PTFE ratio of 34:1 and lubricant at an amount 30% by weight of the particle weight. The mean pore size was 2.45. The composite filtered one liter of water in 4.23 minutes. These zirconia particles have a lubricant absorptive capacity about 25 percent of particle weight.

Various modifications and alterations of this invention will become apparent to those skilled in the art without departing from the scope and spirit of this invention, and it should be understood that this invention is not to be unduly limited to the illustrative embodiments set forth herein.

We claim:

1. A method for controlling porosity and mean pore size in a composite sheet comprising the steps of:
   a) admixing lubricant with a blend comprising insoluble, non-swellable, sorptive particles and polytetrafluoroethylene to form a soft dough-like mass, the lubricant being present in an amount to exceed the sorptive capacity of the particles by at least 3 weight percent, said mass having a cohesive consistency, and the ratio of insoluble particles to PTFE being in the range of 40:1 to 1:4;
   b) intensively mixing said mass at a temperature and for a time sufficient to cause initial fibrillation of said PTFE particles;
   c) biaxially calendering said mass between gaps in calendering rolls maintained at a temperature and for a time, while closing the gap between the calendering rolls with each successive calendering operation, to cause additional fibrillation of said PTFE particles to form a self-supporting tear-resistant sheet having a void volume in the range of 30 to 80 percent and a mean pore size in the range 0.3 to 5.0 micrometers, wherein said void volume and mean pore size vary directly with and are controlled by the amount of lubricant present during processing.

2. The method according to claim 1 further comprising the step of removing lubricant from the resultant sheet to provide a composite sheet comprising a network of interlaced microfibrous PTFE forming a fibril matrix having enmeshed therein said sorptive particles.

3. The method according to claim 1 wherein said lubricant is water or water-based solvent.

4. The method according to claim 1 wherein said lubricant is organic solvent.

5. The method according to claim 1 wherein said lubricant exceeds the lubricant sorptive capacity of particles by an amount in the range of 3 to 200 weight percent.

6. The method according to claim 1 wherein said lubricant exceeds the lubricant sorptive capacity of particles by an amount in the range of 25 to 200 weight percent.

7. The method according to claim 1 wherein said lubricant exceeds the lubricant sorptive capacity of particles by an amount in the range of 40 to 150 weight percent.

8. The method according to claim 1 wherein said particles are carbon, an organic compound or polymer.

9. The method according to claim 1 wherein said particles are an inorganic oxide.

10. The method according to claim 9 wherein said inorganic oxide is selected from the group consisting of silica, alumina, titania, zirconia, and combinations thereof.

11. The method according to claim 1 wherein said particles are ion exchange or chelating particles.

12. The method according to claim 1 wherein said particles comprise a support having an insoluble sorptive coating thereon.

13. The method according to claim 1 wherein said particles have sizes in the range of 0.1 to 200 micrometers.

14. The method according to claim 1 wherein said sorptive particles are silica, said lubricant is water which is present in the range of 103 to 200 weight percent.

15. The method according to claim 1 wherein said blend further comprises more than 0 and up to 28.99 parts per part PTFE of non-swellable property modifiers, provided that the total particles do not exceed 29 parts particles to 1 part PTFE.

16. The method according to claim 15 wherein said property modifiers are cellulosics.

17. The method according to claim 1 wherein said void volume is in the range of 40 to 70 percent.

18. The method according to claim 1 wherein said composite sheet has a mean pore size in the range of 0.5 to 5.0 micrometers.

19. The method according to claim 1 wherein at least 90 percent of pores have a size less than 3.6 micrometers.

20. The method according to claim 1 including tailoring the composite sheet to be useful in at least one of separation applications, diagnostic applications, environmental extraction applications, and clinical extraction applications.

* * * * *

UNITED STATES PATENT AND TRADEMARK OFFICE
CERTIFICATE OF CORRECTION

PATENT NO. : 5,071,610
DATED : December 10, 1991
INVENTOR(S) : Donald F. Hagen et al.

It is certified that error appears in the above-identified patent and that said Letters Patent is hereby corrected as shown below:

On the title page, under "U.S. Patent Documents", "3,556,161  8/1966" should read -- 3,556,161  8/1965 --.

Col. 8, line 15, insert -- . -- after "1 micrometer".

Col. 12, line 8, insert -- . -- after "42".

Col. 16, line 13, "removal" should read -- removable --.

Col. 16, line 14, "(be extraction/leaching) should read -- (by extraction/leaching) --.

Col. 17, line 67, "sorptive" should read -- sorption --.

Col. 19, line 28, this should not be a new paragraph.

Signed and Sealed this

Twelfth Day of October, 1993

*Attest:*

BRUCE LEHMAN

*Attesting Officer*     *Commissioner of Patents and Trademarks*